United States Patent [19]

Segalowitz

[11] Patent Number: 4,981,141
[45] Date of Patent: Jan. 1, 1991

[54] WIRELESS ELECTROCARDIOGRAPHIC MONITORING SYSTEM

[76] Inventor: Jacob Segalowitz, 279 S. Beverly Dr., #1036, Beverly Hills, Calif. 90212

[21] Appl. No.: 310,660

[22] Filed: Feb. 15, 1989

[51] Int. Cl.⁵ .............................................. A61B 5/04
[52] U.S. Cl. ................................. 128/696; 128/903; 128/710; 364/413.060
[58] Field of Search ........ 128/969, 710, 903, 635–641, 128/648, 644; 364/413.06

[56] References Cited

U.S. PATENT DOCUMENTS

| | | | |
|---|---|---|---|
| 2,298,125 | 10/1942 | Hartman | 128/639 |
| 2,660,165 | 11/1953 | Miller | 128/696 |
| 3,757,778 | 9/1973 | Graham | 128/696 |
| 3,848,582 | 11/1974 | Milani et al. | 128/639 |
| 3,858,576 | 1/1975 | Dehnert et al. | 128/712 |
| 3,882,277 | 5/1975 | DePedro et al. | 172/2 DP |
| 3,908,641 | 9/1975 | Judson et al. | 128/710 |
| 4,121,573 | 10/1978 | Crovella et al. | 128/903 |
| 4,356,486 | 10/1982 | Mount | 128/903 |
| 4,593,284 | 6/1986 | Clifford et al. | 340/870.18 |
| 4,606,352 | 8/1986 | Geddes et al. | 128/702 |
| 4,622,979 | 11/1986 | Katchis et al. | 128/702 |
| 4,658,831 | 4/1987 | Reinhard et al. | 128/903 |
| 4,742,831 | 5/1988 | Silvian | 128/710 |
| 4,784,162 | 11/1988 | Ricks et al. | 128/903 |
| 4,827,943 | 5/1989 | Bornn et al. | 128/668 |

FOREIGN PATENT DOCUMENTS 0006447  11/1987  PCT Int'l Appl. ................. 128/696

Primary Examiner—Lee S. Cohen
Assistant Examiner—Scott M. Getzow
Attorney, Agent, or Firm—Burns, Doane, Swecker & Mathis

[57] ABSTRACT

An electrocardiographic monitoring system in which the heart-signal sensing electrodes are each coupled to the heart-signal monitor/recorder by respective wireless transmitters and corresponding respective receiving wireless receivers in a base unit, each transmitter-receiver combination operating (in the absence of an encoding system) at a separate radio frequency, a zero or reference signal being developed at the base unit and being used to modulate a signal transmitter at the base unit, such modulated signal being received and demodulated by a receiver carried by a right-leg electrode carried by the right leg of the patient.

23 Claims, 3 Drawing Sheets

WIRELESS ELECTROCARDIOGRAPHIC MONITORING SYSTEM

1. Field of the Invention

This invention relates to medical instrumentation and, more particularly, to electrocardiographic and cardiocirculatory monitoring equipment.

2. Prior Art

Every muscle can perform only one movement; the shortening of its fibers by contraction. This also applies to the heart muscle. Every action of a muscle has associated with it an electrical activity which changes in the course of the contraction. The electrical signal thus associated with the muscle action is transmitted through various tissues and ultimately reaches the surface of the body. There such electrical signals can be detected by electrodes applied to the skin. Thus, such signals that are being detected by the electrodes can be recorded with the aid of suitable electrocardiographic equipment or can be observed in/or recorded with a monitor/recording unit. The record thus obtained is called an electrocardiogram or a rhythm-monitoring strip.

As early as 1855 action currents from the heart were recorded, as measurements were being made of a beating frog heart. The first actual recording of a frog electrocardiogram was made by A. D. Waller in 1887. The first recording of a human heart electrical action signal (hereinafter the "heart-signal") was made by A. D. Waller in 1889. Modern electrocardiograph, however, started with Einthoven, who invented the string galvanometer (and is credited with the bipolar lead triangle setting for recordings of standard limb leads I, II, III) and applied it to recording small voltages of short duration, which is the category into which heart-signals fall. His recording techniques have not been improved upon very much since they were first published many years ago. Here it should be noted that the term "lead" as used herein is being used in the medical sense and not the electronic sense (i.e., "lead" is a spatial position at which the heart-signal is viewed, not a wire).

After Einthoven's work, the entire field of research stagnated for nearly 30 years until the introduction by Wilson of upper and lower extremities' local leads and the zero electrode used in unipolar recordings. The entire 12-lead system is fed by unipolar and bipolar signals. Unipolar leads are divided into unipolar extremity or limb leads and unipolar precordial or chest leads.

In unipolar limb leads the three extremity leads are;

aVR—the unipolar right arm lead, (R designating the right arm);

aVL—unipolar left arm lead (L designating left arm); and, aVF—unipolar left leg lead, in all of which the "a" stands for "augmented".

The unipolar chest leads are designated by the letter V followed by a subscript numeral which represents the exact location on the chest. In a standard setting there are six precordial leads V1-V6.

In standard limb bipolar leads, lead I is the potential difference between the arms, i.e. left arm potential minus right arm potential. Lead II is the potential difference between the left leg potential and the right arm potential. Lead III is the potential difference between the left leg and the left arm. If the leads are diagrammed on the body they inscribe, essentially, an equilateral triangle. The electrocardiograph generates the lead voltages from the potentials applied to it from the bipolar electrodes. The term "lead" as used in electrocardiography means "view" of the heart's electrical impulse. That "view" varies between leads.

The electrocardiograph is widely used by the medical profession. The standard electrocardiograph requires at least 10 wires to be attached to the body of the patient at one end, and to the electrocardiograph at the other end to detect heart-signals and transform them into a 12 lead electrocardiogram evaluation. This involves attaching six electrodes to the chest or precordial area to obtain recordings of leads V1-V6 as well as attaching 4 electrodes, the arms and legs of the patient to obtain recordings of leads I, II, III, AVR, AVL, AVF. Only three electrodes and three terminal wires are applied to the chest for heart rhythm monitoring. After the ten electrodes are attached to the patient, ten specific wires must be connected between each specific electrocardiograph terminal and the related electrode of predetermined position.

Many and frequent difficulties exist and cumbersome operation of the conventional system arises because of the following factors:

1. Terminal wires from the electrocardiograph have to be connected to the distal electrodes in a pre-determined order. (Defined limb and side to defined wire, as well as specific precordial points to defined precordial wires.) In practice there are relatively frequent errors of connection between a specifically positioned electrode and the specifically associated wire from the electrocardiograph.

2. Often, the 10 terminal wires become intertangled with each other and it takes precious time to get them untangled.

3. When the electrocardiograph is to be operated by an Intensive Coronary Care Mobile Unit, which operates in relatively abnormal conditions, often speed of utilization of the system is crucial since life-threatening situations are involved. In this environment the existing electrocardiographic system exhibits low efficiency and low effectiveness.

4. Since the terminal wires are re-used, if they have any manufacturing defects inherent in them or develop such defects with use throughout their long extent (defects often difficult to detect), operation of the system, (the electrocardiograph or monitor), is unsatisfactory.

5. During surgical procedures the patient is monitored for arrhythmias. Often the wires which extend beneath or beside the sterile field become disconnected from the electrodes during the procedure and it is difficult, out of the sterile surgical field, to reconnect the necessary wires. It is also time consuming and interruptive of the procedure.

6. During hospitalization, rhythm-monitored patients occasionally are permitted to ambulate within the department area. Often the patient disconnects the wires connected from the bedside monitor to the electrodes in order to take a walk or visit the restroom in the area. During this period no rhythm monitoring is possible.

Therefore, it is an object of this invention to overcome the problems previously experienced in connection with application of electrocardiographs in the taking of electrocardiograms and in connection with the rhythm monitoring of patients.

It is a further object of this invention to provide electrocardiographic and rhythm monitoring systems in which the physical wires between the patient and the electrocardiograph or monitor are eliminated.

SUMMARY OF THE INVENTION

A novel, wireless, two-sectioned system having a plurality of microchipped, self-contained and self-powered heart-signal sensing, amplifying, encoding and R-F transmitting, detecting electrodes and a receiving, demodulating and decoding base unit capable of developing in real time, signal-averaging electrocardiography for a 12-lead digital and/or analog interpretive electrocardiogram and/or for rhythm monitoring (on any Holter system) with 3-electrode digital and/or analog interpretive display or recording and/or for obtaining a 12-lead ECG from only three electrodes positioned on the chest for use with existing monitors and display devices.

The electrocardiac activity information detected and transmitted by the system conforms to all professional standards and levels of accuracy for vector progression, duration, intensity and form characteristics, specifically with respect to the following features:

1. Rhythm
2. Rate
3. P wave
4. P-R interval
5. QRS interval
6. QRS complex
7. ST segment
8. T wave
9. U wave
10. Q-T duration The system will function within a nominal range of 150 feet between the electrode system and the base unit and will be suitable for operation with a single-channel or multi-channel electrocardiograph, monitor or Holter, fixed, A-C operated or portable, battery operated or any combination thereof. The receiving-demodulating-decoding base unit used with the system can be connected to existing, stand-alone electrocardiographs or, by reason of its miniature size, can be integrated into new generations of such machines. Interference between multiple systems operating in the same facility is prevented by choosing different center frequencies for the different systems.

The electrodes may be circular with concentric outer ring and center skin contacts, the outer ring being the reference potential contact to the body of the patient. Alternatively, an elongated electrode with separated contacts may be used, one being the signal or pick-up contact and the other being the reference or zero potential contact.

While reference has been made herein to an R-F system of coupling between body electrodes and the base unit, it should be understood that, with the proper operating environment, ultrasonic or laser technologies may be used.

The left arm, right arm and left leg limb signals are fed in unipolar fashion to a bridge or "Wilson" network in the base unit to derive a reference signal for application to the right leg reference or "indifferent" electrode. That reference signal is used to modulate an F-M transmitter at the base unit. At the right leg electrode, a battery operated receiver detects, de-codes and amplifies the "indifferent" or reference signal and applies it to the right leg through a two-contact electrode to complete the signal path in the system. Alternatively, a balanced, mixed combination of the left arm, right arm and left leg signals is radiated from the base unit to the right leg R-F receiver electrode which applies such combination signal to the right leg.

Referring to bipolar lead recordings, the electrodes function in the same wireless fashion, with the switchable characteristic of each electrode permitting identification of the location of that electrode so that the proper combination of limb signals is utilized in the ECG to develop I, II, and II leads.

Similarly, the precordial electrodes V1–V6, according to this invention, are coupled, in wireless fashion, to appropriate, respective channels in the base station for processing and use.

BRIEF DESCRIPTION OF THE DRAWINGS

This invention and its advances over the prior art can best be understood by reading the Specification which follows in conjunction with the drawings herein, in which.

DETAILED DESCRIPTION OF THE PREFERRED EMBODIMENT

Figures 1, 1A:
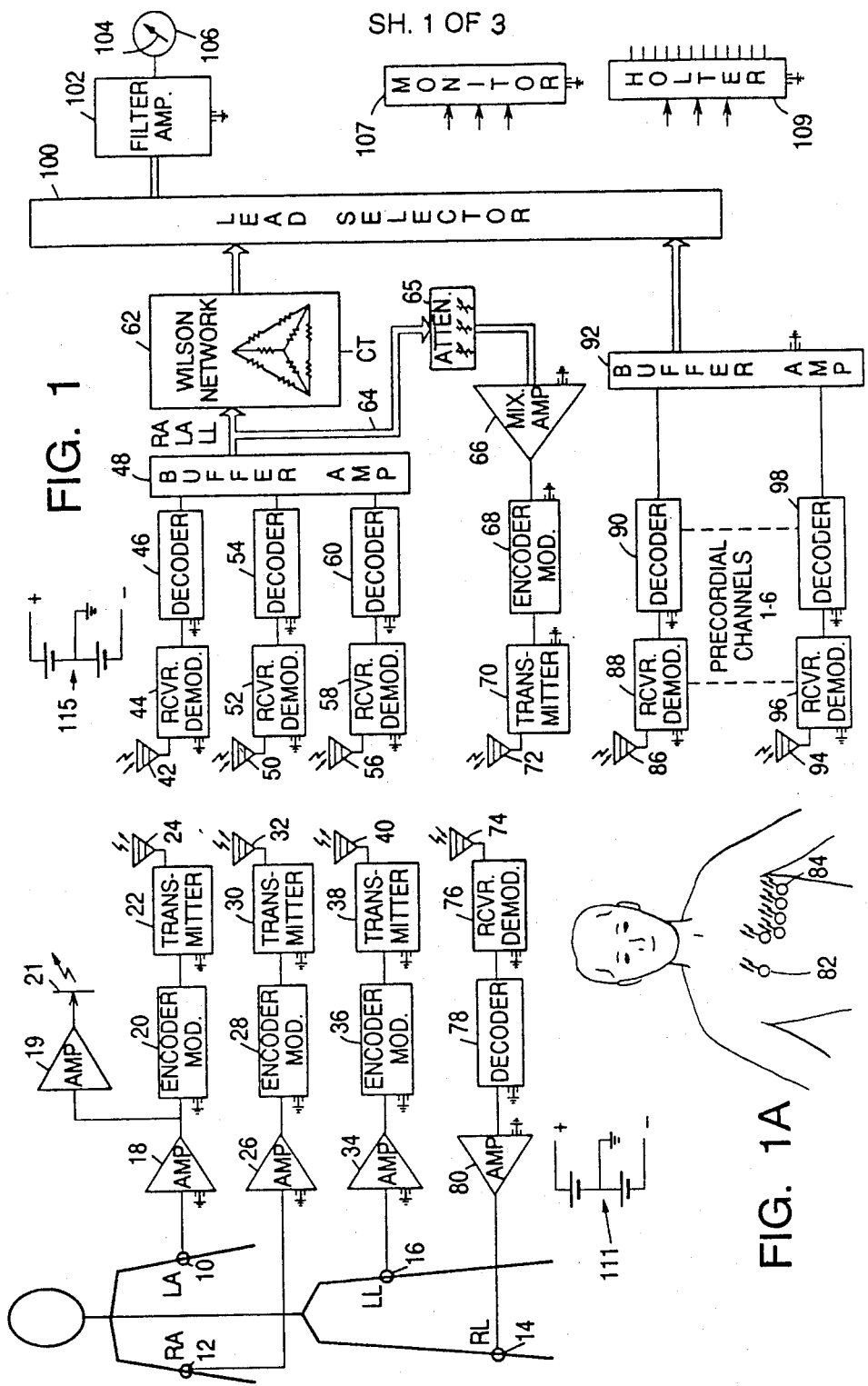
FIG. 1 is a block diagram of a wireless electrocardiograph system, according to the present invention.
FIG. 1A is a graphical representation of the distribution of additional electrodes in the system of FIG. 1.

In FIG. 1, the human body is represented by a stick figure as far as the location of limb electrodes of the system is concerned. Electrode 10 is connected to the left arm, electrode 12 is connected to the right arm, electrode 14 is connected to the right leg and electrode 16 is connected to the left leg. Each of these electrodes may be the concentric type shown in FIG. 2 with the outer conductive strip being used to establish a localized zero or reference potential and the center connector being the source of signal for transmission or the point of application of the signal in the receiving mode. The outer ring may be referred to as an "indifferent" electrode of a localized nature. In the precordial area the electrode of FIG. 6 may be used.

The output signal from electrode 10 is fed to amplifier 18 which feeds encoder-modulator 20. The signal thus derived is used to modulate transmitter 22 which is connected to antenna 24 from which the modulated RF signal is radiated. Amplifier 18 may comprise a microchip-type RC 4560 which has a dual stage operational amplifier. Encoder modulator 20 may comprise a CM 8555 IPA, or equivalent, in combination with a 40H393 chip. If digital encoding is utilized a single transmitting frequency may be used for all transmitters. However, if analog modulation by the signal from electrode 10 is utilized, encoder modulator 20 may act merely as a modulator and each of the transmitters may be set at a different center frequency. Transmitter 22, and corresponding transmitters in other channels, may comprise a 930F5 micro-chip which includes a Colpitts oscillator.

The audio frequency range which must be reproduced by the system is 0.05 Hz to 125 Hz. The F-M swing of the carrier frequency is 40% of the carrier frequency.

As shown, the output of amplifier 18 may also be fed through an additional amplifier 19 to an LED 21 which will give a light pulse each time a heart-signal is received at electrode 10. This heart-signal indicator may be provided at each electrode, if desired.

The heart-signal from electrode 12 is fed to an amplifier 26, which, again, is a high gain, low noise amplifier and the output of amplifier 26 is fed to encoder modulator 28 and, thence, to transmitter 30. The output of transmitter 30 is fed to antenna 32 for radiation.

The heart-signal from left leg electrode 16 is fed to amplifier 34 and, the output of that amplifier 34 is fed to encoder-modulator 36 for modulating F-M transmitter 38. The output of transmitter 38 is fed to antenna 40 for radiation.

The signal radiated by antenna 24 is intercepted by antenna 42 and fed to receiver demodulator 44, the output of which is fed to decoder 46 and, thence, to buffer amplifier 48.

The signal from antenna 32 is intercepted by antenna 50 and fed to receiver-demodulator 52 the output of which is fed to decoder 54 and, thence, to buffer amplifier 48.

Similarly, the signal from antenna 40 is received by antenna 56 and that signal is demodulated in receiver-demodulator 58 which feeds its output signal to decoder 60 for application to buffer amplifier bank 48. It should be understood that in buffer amplifier bank 48 there is a series of amplifiers, one for each limb signal channel. The signals from buffer amplifier 48 are fed to what is known as a "Wilson" network. This is essentially a bridge, the make up of which can be seen in FIG. 3. The left arm, right arm and left leg signals are coupled to the "Wilson" network to produce what is known as an "indifferent" or reference potential which appears at terminal CT. In this embodiment the signal at CT is not used but it is used in the embodiment of FIG. 4. Instead, here, the right arm, left arm and left leg signals are fed to a balancing attenuator 65 and, thence, to a mixer amplifier 66 where the mixed signal is amplified by a low noise, high gain amplifier 66 and results in the modulation by encoder-modulator 68 of transmitter 70 which is coupled for RF purposes to antenna 72 and the RF signal, thus modulated, is radiated by antenna 72. The radiated reference signal is picked up by receiving antenna 74 such antenna being coupled to receiver demodulator 76 which develops a signal in the audible or sub-audible frequency range. Such signal, if it is encoded, may then be decoded by decoder 78 and the resulting signal may be applied to amplifier 80 which is coupled to the active element of electrode 14 carried by the right leg. This establishes the so-called "zero" potential on the "indifferent" or reference electrode 14. Such a "zero" signal is necessary for operation of a system involving the use of unipolar limb leads. The signals from the same electrodes are used to produce the bipolar limb leads previously described.

Figure 5:
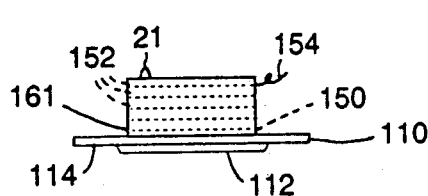
FIG. 5 is an elevational view of the concentric electrode of FIG. 2.

The transmitters in the system, if purely analog techniques are involved, may be set at center frequencies of, for example, 72.080 MHz and at multiples of 160 KHz around that center frequency. The transmitters operate simultaneously but with 160 KHz separation there is no problem with intermodulation at the respective receivers. Operation at much higher frequencies, for example in the 400 MHz band, results in a requirement for a much shorter antenna but increases power requirements, thus putting a heavier load on the very small battery which can be mounted with the micro-chips in connection with the electrodes utilized in the system, as shown in FIG. 5. This analysis applies equally to electrodes used to detect signals for unipolar or bipolar leads. With a digitally encoded system, the center frequency may also be changed between systems to reduce the possibility of interference between systems operating in proximity to each other.

As for the heart-signals at the precordial electrodes, such as electrode 82 and electrode 84, the transmitters are as shown in connection with the limb signal transmitters, just described. Again the frequencies are set differently, each from the other but, at higher frequencies, this is not a problem. Also, because the field strength of the signals from the various electrodes associated with transmitters is low, there is considerable freedom in choosing a frequency which is free of local interference. There are generally six precordial electrodes and, therefore, in this system there are six precordial channels, each having the transmitting and receiving structures of corresponding elements in the unipolar limb signal channels. For example, the signal from electrode 82 and its associated transmitter is received by antenna 86 and is fed to receiver-demodulator 88 where a signal in the audible or sub-audible frequency range is obtained and fed to decoder 90 for any decoding that is necessary to reproduce the heart-signal. The heart-signal thus derived is applied to buffer amplifier bank 92. Similarly, the heart-signal detected at electrode 84 is transmitted by the associated transmitter and is received by antenna 94, following which it is detected and demodulated by receiver demodulator 96 and, if necessary, it is decoded by decoder 98 and fed to buffer amplifier 92. Buffer amplifier 92 is a bank of amplifiers, one for each precordial signal channel. The unipolar limb signals and the precordial signals are fed, without loss of integrity, to lead selector 100 which is of the conventional type found in electrocardiographs and which permit selection of each of the channels individually. The output of lead selector 100 is fed to filter-amplifier 102, following which the signal is fed to the electrocardiographic analog or digital cardiographic display. The analog recording pen is represented by needle 104. The galvanometric mechanism is represented by element 106. Alternately, three of the signals shown entering lead selector 100 may be fed directly to a monitor 107 or to a Holter system for developing a 12-lead electrocardiogram from the signals sensed by three electrodes placed only on the chest area.

Figure 2:
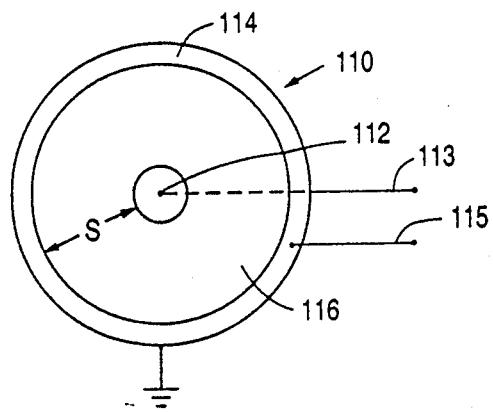
FIG. 2 is a schematic diagram of a concentric electrode for use in the present invention.

Turning to FIG. 2, signal contact element 112 is electrically conductive in nature and has a conductor 113 associated therewith for coupling to the micro-chip amplifier, encoder-modulator, transmitter element of FIG. 1, or to external equipment. Contact 112 may be of aluminum, for example. Contact 114 is the "indifferent" or reference contact for electrode 110. The spacing "S" between contact 114 and contact 112 may approximate 1½ to 2 inches. Of course, concentric ring contact 114 is electrically conductive in nature. In some cases it may not be a closed circle but may merely be an arc of a circle. Contacts 112 and 114 are carried on a plastic film material 116, for example. If contacts 114 and 112 are too widely separated the accuracy of the graphic reproduction of the heart-signal will be diminished.

Figure 3:
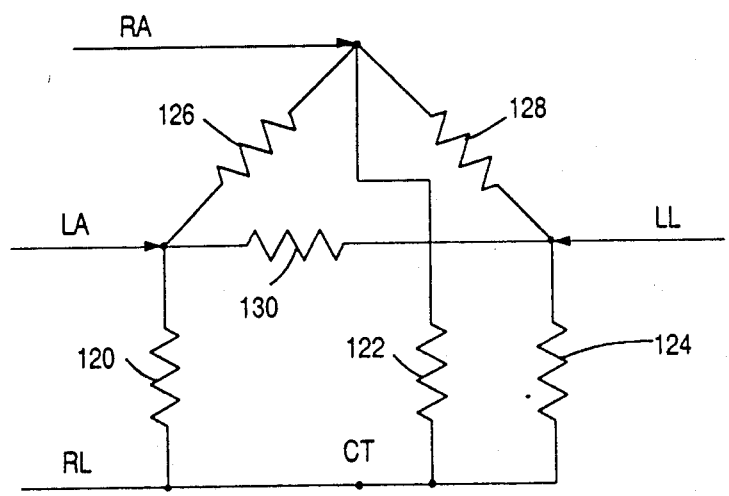
FIG. 3 is a schematic diagram of a "Wilson" network or bridge for developing an "indifferent" signal.

In FIG. 3 the so-called "Wilson" network is shown. The purpose of this network is to establish a "zero" area of the field from the heart dipole which is creating the field being studied. As can be seen from FIG. 3, the right arm, left arm and left leg potentials are combined through three equal resistors, 120, 122 and 124 to establish a "zero" or reference point which is generally referred to as the "central terminal". The size of resistors 120, 122 and 124 is in excess of 5000 ohms with the general range being 5000–15,000 ohms. The central terminal ("CT") potential is not actually "zero". Theoretically, the potential of the CT terminal is the mid-dipole potential of the heart-signal generator if the field is homogenous and if the dipole generating the signal lies exactly in the center of an equilateral triangle, the angles of which are formed by the three electrode points LA, RA, LL. Resistors 126, 128 and 130 have the same resistance and form an electrical equilateral triangle simulating the Einthoven triangle of the electrocardiographic art.

Figure 4:
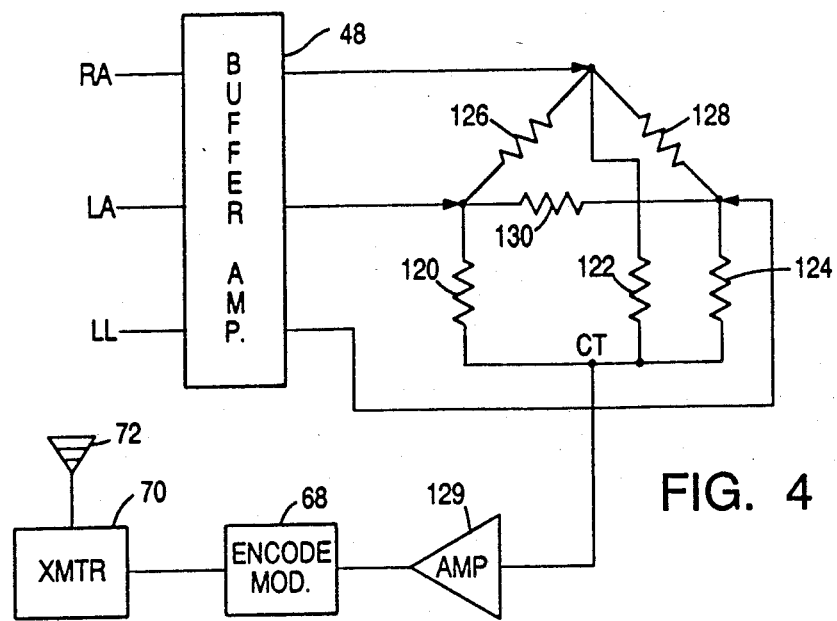
FIG. 4 is a schematic diagram of an alternative circuit for developing a right leg signal.

According to the embodiment of FIG. 4, the CT potential is, after amplification by amplifier 129, transmitted by transmitter 70 through antenna 72 to receiver-demodulator 76 and its associated components for application to the right leg electrode 14, shown in FIG. 1.

Unipolar leads are presently the only ones used in the precordial positions, shown in FIG. 1A. It was formerly believed that a limb could serve for the "indifferent" or reference connection because it was relatively so distant from the precordial electrode. It soon became apparent, however, that this was not the case, that the arm or leg was not truly "indifferent" and it altered the results in varying degrees depending on which limb was connected to the negative terminal of the electrocardiograph. Thus, the need for establishing a central terminal, as described hereinbefore.

Associated with each of the limb and precordial electrodes is a power supply 111 (conventionally a battery) which provides to the micro-chips operating voltage of the necessary sign and magnitude. At the base station side IC operating voltage of the necessary sign and magnitude is provided by power supply 115 which may be battery or A.C. based.

From FIG. 5, it is apparent that each electrode patch 110 carries its own power supply 150 as well as the necessary micro-chips 152, which are powered by power supply 150, and an antenna 154. An LED 21 may also be provided which lights with each heart beat. Tab 161 is an insulating member which, when pulled, connects power supply 150 to the micro-chips and turns "on" the associated electrode. This is true for the receiving electrode 14 on the right leg as well as for the various transmitting electrodes.

Figure 6:
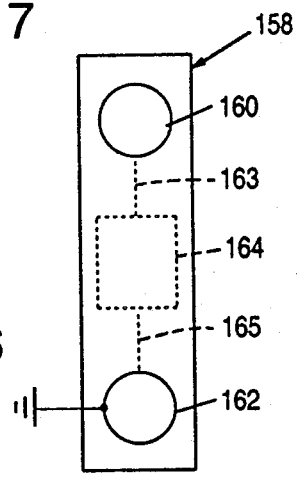
FIG. 6 is an elevational view of an alternative form of electrode.

FIG. 6 shows an alternative form of electrode structure 158 which is particularly useful for precordial application. The necessary separation of signal electrode 160 and zero reference electrode 162 is achieved in the limited space available on the chest. This strip electrode structure carries a micro-chip amplifier, encoder-modulator and transmitter module 164 (with battery) and connectors 163, 165 for signal input.

To limit the number of electrodes with different operating parameters which must be kept in inventory and employed in setting up the system for a given patient, each electrode may have a multiple-position switch which changes the frequency or digital encoding of the signal from the electrode so that it matches that parameter for the site at which it is to be used on the patient.

The electrodes may be color coded to indicate where they should be placed on the body. They may also include frequency or code switches to permit one electrode type to be usable in various body locations.

Figure 7:
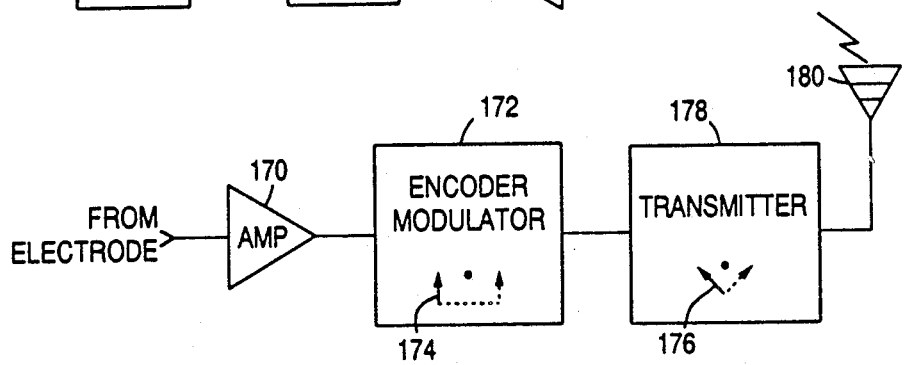
FIG. 7 is a block diagram of an electrode with switchable code and transmitter frequency.

FIG. 7 illustrates, in block form, this capability. In FIG. 7, heart-signals from any of the 10 electrodes is coupled to amplifier 170, as shown in FIG. 1. The output of amplifier 170 is fed to encoder/modulator 172 which includes a quad NAND gate section, as is found, for example, in a type TSC-323 integrated circuit. DIP switch 174 permits selection of a 3-digit code, if digital encoding is used. On the other hand, if analog encoding is to be used, a frequency-change switch 176 is provided on transmitter 178. The oscillators described in connection with FIG. 1 (which are used here) are tunable by changing the applied voltage. Such voltage change is accomplished by switch 176. Thus, by either method, the number of different types of electrodes that must be inventoried can be reduced. The base station decoders or receiver-demodulator may be fixed and the electrode encoding means may be adjusted to correspond to the code or frequency of a target signal channel at the base station.

The appropriately encoded signal, or the signal at the desired frequency is fed to antenna 180.

This system is adapted to work with Holter systems in which 12-lead electrocardiograms are derived from three-electrode information. This fact is illustrated by element 109 in FIG. 1.

While a particular embodiment has been shown and described, it will be apparent to those skilled in the art that variations and modifications may be made in that embodiment without departing from the spirit and scope of this invention. It is the purpose of the appended Claims to cover any and all such variations and modifications.

I claim:

1. A wireless electrocardiographic monitoring system for displaying detected heart-signals, said system including:

right arm, left arm, right leg and left leg electrodes for attachment to the indicated limbs of a patient;

right arm heart-signal transmitting means electrically couplable to said right arm electrode for radiating a signal corresponding to the heart-signal at said right arm electrode;

left arm heart-signal transmitting means electrically couplable to said left arm electrode for radiating a signal corresponding to the heart-signal at said left arm electrode;

left leg heart-signal transmitting means electrically couplable to said left leg electrode for radiating a signal corresponding to the heart-signal at said left leg electrode;

a plurality of signal receiving means, one each for receiving and detecting said radiated heart-signals from said left arm, right arm and left leg electrodes, respectively, to individually produce a received left arm heart-signal, a received right arm heart-signal and a received left leg heart-signal;

means for combining said individually received left arm, right arm and left leg heart-signals to produce a reference potential;

reference potential transmitting means coupled to said combining means for transmitting said reference potential;

right leg signal receiving means electrically couplable to said right leg electrode for receiving said reference potential and applying said reference potential to said right leg electrode;

a set of precordial electrodes for attachment to the chest of a patient;

a set of precordial heart-signal transmitting means each one electrically couplable to different ones of said precordial electrodes in said set for individually radiating signals corresponding to the heart-signal at respective ones of said precordial electrodes;

a set of precordial heart-signal receiving and detecting means, each one associated with a different one of said precordial heart-signal transmitting means for individually reproducing the heart-signals appearing at each of said precordial electrodes in said set;

signal display means;

means for coupling said detected heart-signals from said right arm, left arm and left leg electrodes and from said precordial electrodes to said signal display means; and means for providing operating power for all of the foregoing.

2. The system according to claim 1 in which each of said electrodes comprises first and second conductive elements in spaced relationship to each other.

3. The system according to claim 1 in which said combining means is a Wilson network.

4. The system according to claim 3 in which said Wilson network includes three resistors electrically joined at one end, each such resistor having a resistance in excess of 5000 ohms.

5. The system according to claim 1 in which said signal display means is a monitor.

6. The system according to claim 1 in which said heart-signal transmitting means includes an FM transmitter.

7. The system according to claim 1 in which said means for combining said left arm, right arm and left leg heart-signals includes an attenuator and a mixer amplifier.

8. The system according to claim 1 in which said means for applying operating power includes a battery and battery switching means in each of said left arm, right arm, left leg and precordial transmitting means, and said right leg signal receiving means.

9. The system according to claim 8 in which said battery switching means includes a removable insulator which when present maintains the battery disconnected from the associated transmitter and receiver means.

10. The system according to claim 1 further including an LED and LED driver as part of each of said left arm, right arm, left leg and precordial transmitting means for indicating the presence of signals.

11. The system as in claim 1 wherein each of said electrodes is disposable.

12. The system as in claim 1 wherein the combination of each of said electrodes and its associated transmitter or receiver is disposable.

13. A wireless electrocardiographic monitoring system for displaying detected heart-signals, said system including:

right arm, left arm and left leg electrodes for attachment to the indicated limbs of a patient;

right arm heart-signal transmitting means electrically couplable to said right arm electrode for transmitting a signal corresponding to the heart-signal at said right arm electrode;

left arm heart-signal transmitting means electrically couplable to said left arm electrode for transmitting a signal corresponding to the heart-signal at said left arm electrode;

left leg heart-signal transmitting means electrically couplable to said left leg electrode for transmitting a signal corresponding to the heart-signal at said left leg electrode;

a plurality of signal receiving means, one each for receiving and detecting said transmitted heart-signals from said left arm, right arm and left leg electrodes to individually produce a received left arm heart-signal, a received right arm heart-signal and a received left leg heart-signal;

network means for combining said individually received left arm, right arm and left leg heart-signals to produce bipolar heart leads;

a set of precordial electrodes for attachment to the chest of a patient;

a set of precordial heart-signal transmitting means, one each electrically couplable to different ones of said precordial electrodes in said set for individually transmitting signals corresponding to the heart-signal at respective ones of said precordial electrodes;

a set of precordial heart-signal receiving and detecting means, each one associated with a different one of said precordial heart-signal transmitting means for individually reproducing the heart-signals appearing at each of said precordial electrodes in said set;

means for providing operating power for all of the foregoing; and means for selectively providing said bipolar heart leads, said detected heart-signals from said right arm, left arm and left leg electrodes, and the signals from said precordial electrodes to be coupled to an electrocardiographic recorder.

14. The system according to claim 13 in which said combining means is a Wilson network.

15. The system according to claim 14 in which said Wilson network includes three resistors each connected at one end to the other two resistors, the resistance of each such resistor being in excess of 5000 ohms.

16. The system according to claim 13 in which said means for selectively providing said bipolar heart leads to an electrocardiographic recorder is a lead selector.

17. The system according to claim 13 in which said heart-signal transmitting means is an FM transmitter.

18. The system according to claim 13 in which each of said electrodes comprises a central signal contact element and a concentric ring reference element surrounding said central signal contact element.

19. The system according to claim 13 in which said means for applying operating power includes a battery and battery switching means in each of said left arm, right arm, left leg and precordial transmitting means.

20. The system according to claim 19 in which said battery switching means includes a removable insulator which when present maintains the battery disconnected from the associated transmitter means.

21. The system according to claim 13 further including an LED and LED driver as part of each of said left arm, right arm, left leg and precordial transmitting means for indicating the presence of signals.

22. The system as in claim 13 wherein each of said electrodes is disposable.

23. The system as in claim 13 wherein the combination of each of said electrodes and its associated transmitter is disposable.

* * * * *